United States Patent [19]
Yamamoto et al.

[11] Patent Number: 5,674,263
[45] Date of Patent: Oct. 7, 1997

[54] OPTIC NERVE IMAGE OUTPUT DEVICE AND METHOD

[76] Inventors: Hiroshi Yamamoto, 57-3, 6 ban Kouchi, Oaza Hoketsu, Yoshida-cho, Kitauwa-gun, Ehime Pref.; Tooru Ishii, 791,66 Takaoka-cho, Matsuyama, Ehime-Pref., both of Japan

[21] Appl. No.: 617,070

[22] Filed: Mar. 18, 1996

[30] Foreign Application Priority Data

Apr. 26, 1995 [JP] Japan .................................. 7-127203

[51] Int. Cl.$^6$ ........................................... A61N 1/32
[52] U.S. Cl. ................................................. 607/54
[58] Field of Search ........................... 607/54, 2; 623/4

[56] References Cited

U.S. PATENT DOCUMENTS

| | | | |
|---|---|---|---|
| 4,664,117 | 5/1987 | Beck | 607/54 |
| 4,793,353 | 12/1988 | Borkan | 607/54 |
| 4,979,508 | 12/1990 | Beck | 607/54 |

FOREIGN PATENT DOCUMENTS

| | | | |
|---|---|---|---|
| 743764 | 10/1966 | Canada | 128/1 |
| 1943956 | 5/1971 | Germany | A61F 9/08 |
| 2016276 | 9/1979 | United Kingdom | A61N 1/36 |

*Primary Examiner*—William E. Kamm
*Assistant Examiner*—Carl H. Layno
*Attorney, Agent, or Firm*—Moonray Kojima

[57] ABSTRACT

An optic nerve image output device and method for modulating image signals output by an image output device with low-frequency square waves output by a square wave output device and outputting this modulated output at the portion acted upon by optic nerve at the head on the human body side with an output device. If low-frequency square wave signals are applied to the portion acted upon by optic nerve at the head on the human body, the optic nerve can visually feel a square screen by light and scanning lines on that screen. For that reason, if video signals are applied after modification with such low-frequency square wave signals, an image is directly felt by the optic nerve, making it possible for not only healthy persons but also blind persons to recognize the image and thus also making it possible to use the human body as a display.

6 Claims, 1 Drawing Sheet

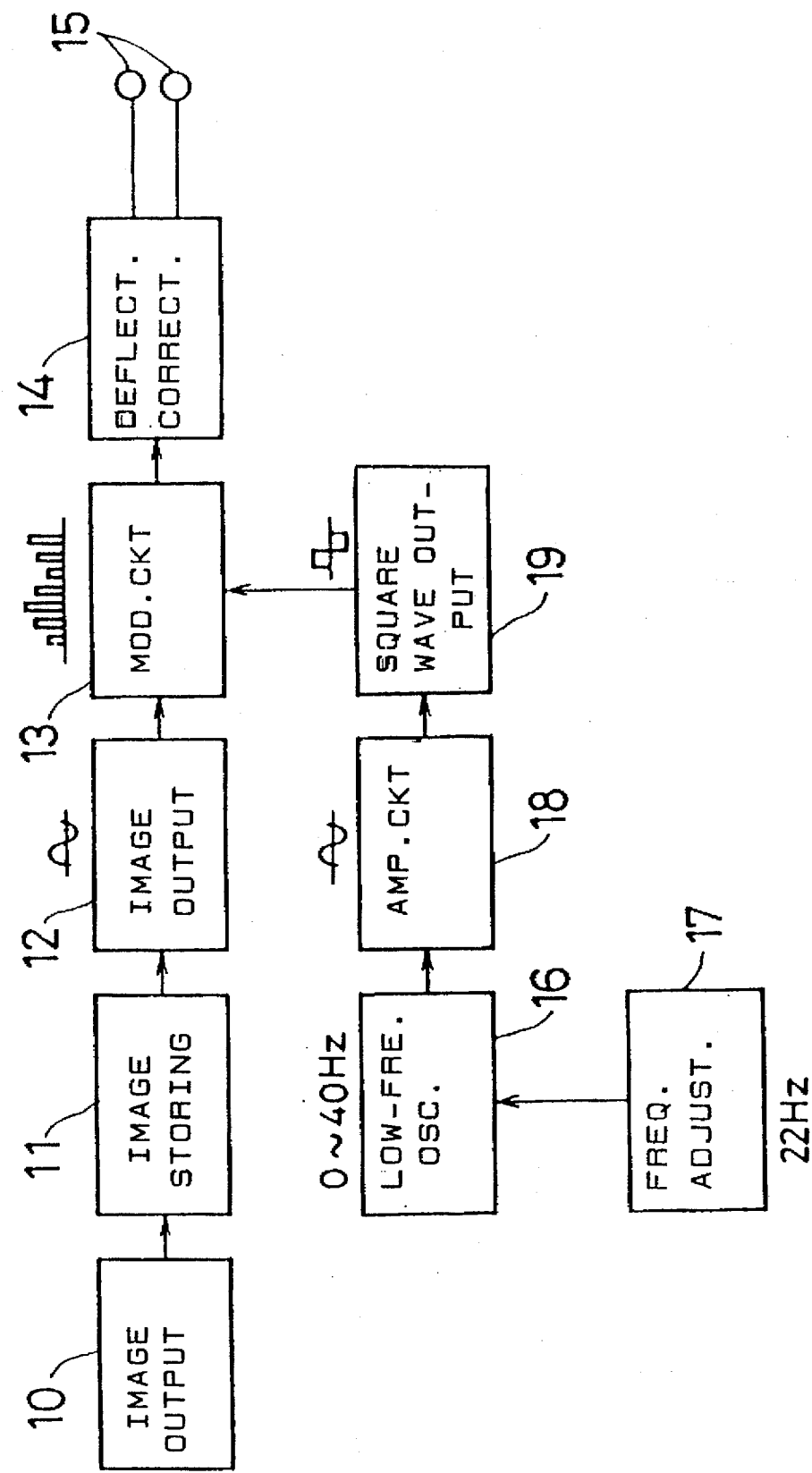

OPTIC NERVE IMAGE OUTPUT DEVICE AND METHOD

BACKGROUND OF THE INVENTION

1. Technical Field of the Invention

This invention relates to an optic nerve image output device capable of visualizing an image (figure) and using human body as display by directly applying video signals to a human body, and a method for it.

2. Description of the Prior Art

Conventionally, there are CRT, liquid crystal, electric discharge tube, etc. as devices for outputting images and, with all those devices, recognition of image (figure) is possible only with the presence of a visual power in the viewer's eyes. However, persons without visual power (disorder of lens system or retina system) cannot recognize the image (figure) from them. Namely, it is difficult for visually handicapped or blind persons to recognize the above-mentioned image (figure).

SUMMARY OF THE INVENTION

The object of this invention is to provide an optic nerve image output device capable of visualizing an image (figure), making it possible for not only healthy persons but also persons without visual power (disorder of lens system or retina system) to recognize the above-mentioned image (figure) and using human body as display by directly applying video signals to a human body, and a method for it.

This invention is characterized in that it is an optic nerve image output device provided with image output means for outputting image signals, square wave output means for outputting low-frequency square waves, modulation means for modulating image signals output by said image output means with low-frequency square waves output by said square wave output means, and output means for outputting signals modulated with said modulation means at the portion acted upon by optic nerve at the head on the human body side.

Moreover, this invention is characterized in that it is an optic nerve image output method for applying video signals to the portion acted upon by optic nerve at the temples on the human body side by modulating them with low-frequency square waves.

If low-frequency square wave signals are applied to the portion acted upon by optic nerve at the head on the human body side, the optic nerve can visually feel a square screen by light and scanning lines on that screen. For that reason, if video signals are applied after modification with such low-frequency square wave signals, the scanning lines visualized on the screen form an image, making it possible to visually recognize that image.

Moreover, in the case where square waves are formed in continuous alternating wave form in which the polarity is alternately switched, an effective light can be obtained visually. Furthermore, when square waves are formed at low frequency of 15 to 25 Hz, an effective luminance (brightness) can be obtained. The image becomes white with excessive luminance and rough at 15 Hz or under but becomes dark with low luminance at 25 Hz or over.

As described above, this invention makes it possible for not only healthy persons but also persons with poor visual power or blind persons to visually recognize images because the images are felt directly with optic nerve and, therefore, enables using human body as display.

BRIEF DESCRIPTION OF THE DRAWINGS

FIG. 1 indicates a structural block diagram of the optic nerve image output device.

DESCRIPTION OF THE PREFERRED EMBODIMENTS

An embodiment of this invention will be described hereafter based on a drawing.

The drawing indicates an optic nerve image output device and, in FIG. 1, the optic nerve image output device 10 is constructed with an equipment capable of outputting video signals such as video camera, laser disc player, "Family Computer", etc., for example, and outputs video signals. The image storage circuit 11 stores the video signals in each visually caught single image and the video signals of this single image turn into a single static image.

The image output circuit 12 takes out the video signals for a single static image from the image storage circuit 11 in the preceding stage and outputs them for a prescribed time or for 2 seconds, for example, and repeats take-out and output of video signals in this cycle. Because storing of image becomes insufficient with a static image under 2 seconds, a static image of 2 to 8 seconds is desirable for obtaining a natural storing state.

The modulation circuit 13 modulates the above-mentioned video signals, with square waves to be described later, into signals which can be visually caught by optic nerve. The deflection correcting circuit 14 is a circuit for correcting the parallelism of scanning lines produced as a vision in the optic nerve and, to be concrete, corrects the scanning lines appearing lower on the right to be parallel. The electrodes 15, 15 are output means for applying modified and corrected video signals to the portion acted upon by optic nerve at both temples of human body.

The low-frequency oscillation circuit 16 oscillates low-frequency signals of 0 to 40 Hz and the frequency adjusting circuit 17 outputs the low-frequency signals of the low-frequency oscillation circuit 16 by adjusting to 22 Hz. The amplification circuit 18 amplifies the low-frequency signals of 22 Hz while the square wave output circuit 19 outputs continuous alternating square waves in which the polarity is alternately switched.

To explain the action of an optic nerve image output device constructed this way, when a low-frequency square wave signal is applied to the portion acted upon by optic nerve at both temples of human body, the optic nerve can feel a stable square screen by light and scanning lines visualized on that screen and, for that reason, if this video signal is applied after modulation with low-frequency square wave signal, the scanning lines form an image, making it possible to visually recognize that image.

The screen of light visually caught by optic nerve is a square of stable shape and the number of scanning lines in this screen is stable in correspondence to the frequency of the square waves. For example, at the frequency of 15 Hz, the scanning lines appear in the number of 15 and, in the same way, in that number of 22 at 22 Hz, 25 scanning lines at 25 Hz and 44 lines at 44 Hz. However, the length (range) of the scanning lines remains the same (fixed value) at any frequency. For that reason, the storage capacity for a single static image of the image storing device 11 is set in correspondence to this number and length of scanning lines.

Namely, as video signals are output from the image output device 10, the image storing device 11 stores the video signals in each visually caught single image and the image output circuit 12 reads the video signals for a single static image from the image storing device 11 every 2 seconds and outputs them for 2 seconds. The modulation circuit 13 modulates the video signals with square waves, while the deflection correcting circuit 14 corrects the parallelism and outputs the signals from the electrodes 15, 15. This output is made at a frequency of 22 Hz, a voltage of 2 V and a current intensity of 100 μA.

The above-mentioned electrodes 15, 15 can apply said video signals to the portion acted upon by optic nerve at both temples of human body by being put in contact with that portion.

As a result, the optic nerve can feel a square screen by light, can further feel scanning lines on that square screen and, because these scanning lines are visualized by video signals, can visually recognize them as an image. And, that recognized image can be visualized like a motion picture fed frame by frame at 2-second intervals. Such visualization of image makes it possible to use human body as display.

As indicated in the above-described embodiment, by forming square waves output from the square wave output circuit 19 in continuous alternating waveform in which the polarity is alternately switched, it is possible to visually obtain an effective light. Moreover, if the square waves are formed with low-frequency waves of 15 to 25 Hz, an effective luminance (brightness) can be obtained. The image becomes white with excessive luminance and rough at 15 Hz or under but becomes dark with low luminance at 25 Hz or over. However, if the frequency is set for 44 Hz, visual recognition of image is possible though inferior in luminance, and the image becomes sharper because the number of scanning lines is 44. For that reason, this can be used when priority is given to sharp image rather than to luminance.

While the image in the aforementioned embodiment is a motion picture sent frame by frame at 2-second intervals, in visualization of ordinary motion picture, it is possible to control the video signals output from the image output device 10 to an output for one scanning line and an output for one image by means of the image output circuit 12.

What is claimed is:

1. An optic nerve image output device comprising:
   image output means for outputting image signals,
   square wave output means for outputting low-frequency square waves,
   modulation means for modulating said image signals outputted by said image output means with said low-frequency square waves outputted by said square wave output means, and
   output means for outputting signals modulated by said modulation means at a portion acted upon by an optic nerve at a head of a human body.

2. An optic nerve image output device comprising:
   image output means for outputting image signals;
   square wave output means for outputting low frequency square waves;
   modulation means for modulating said image signals outputted by said image output means with said low frequency square waves outputted by said square wave output means; and
   output means for outputting signals modulated by said modulation means at a portion acted upon by an optic nerve at a head of a human body; wherein
   said square waves are formed in a continuous alternating waveform in which polarity is alternately switched by a means for alternately switching the polarity of said square waves.

3. An optic nerve image output device comprising:
   image output means for outputting image signals;
   square wave output means for outputting low frequency square waves;
   modulation means for modulating said image signals outputted by said image output means with said low frequency square waves outputted by said square wave output means; and
   output means for outputting signals modulated with said modulation means at a portion acted upon by an optic nerve at a head of a human body; wherein
   said square waves are formed with low frequency waves of 15 to 25 Hz by a means for generating square waves between 15 to 25 Hz.

4. An optic nerve image output method for applying video signals to a portion acted upon by an optic nerve at a head of a human body by modulating said video signals with low-frequency square waves.

5. An optic nerve image output method for applying video signals to a portion acted upon by an optic nerve at head of a human body by modulating said video signals with low frequency square waves; wherein
   said square waves are formed in a continuous alternating waveform in which polarity is alternately switched by a means for alternately switching the polarity of said square waves.

6. An optic nerve image output method for applying video signals to a portion acted upon by an optic nerve at a head of a human body by modulating said video signals with low frequency square waves; wherein
   said square waves are formed with low frequency waves of 15 to 25 Hz by a means for generating square waves between 15 to 25 Hz.

* * * * *